United States Patent
Tang et al.

(10) Patent No.: US 10,428,012 B2
(45) Date of Patent: Oct. 1, 2019

(54) METHOD OF PREPARATION OF 4-ISOPROPYLAMINO-1-BUTANOL

(71) Applicant: SEASONS BIOTECHNOLOGY (TAIZHOU) CO., LTD., Taizhou (CN)

(72) Inventors: Fanghui Tang, Shanghai (CN); Chi Ma, Shanghai (CN); Qiang Jia, Shanghai (CN)

(73) Assignee: SEASONS BIOTECHNOLOGY CO., LTD., Taizhou (CN)

( * ) Notice: Subject to any disclaimer, the term of this patent is extended or adjusted under 35 U.S.C. 154(b) by 0 days.

(21) Appl. No.: 16/146,499

(22) Filed: Sep. 28, 2018

(65) Prior Publication Data

US 2019/0084921 A1    Mar. 21, 2019

Related U.S. Application Data

(62) Division of application No. 15/552,772, filed as application No. PCT/CN2016/000180 on Mar. 31, 2016, now Pat. No. 10,144,701.

(30) Foreign Application Priority Data

Apr. 7, 2015 (CN) .......................... 2015 1 0166233

(51) Int. Cl.
| | |
|---|---|
| *C07C 213/00* | (2006.01) |
| *C07C 213/02* | (2006.01) |
| *C07C 219/06* | (2006.01) |
| *C07C 67/08* | (2006.01) |
| *C07C 67/24* | (2006.01) |

(52) U.S. Cl.
CPC ............ *C07C 213/00* (2013.01); *C07C 67/08* (2013.01); *C07C 67/24* (2013.01); *C07C 213/02* (2013.01); *C07C 219/06* (2013.01)

(58) Field of Classification Search
CPC ... C07C 213/00; C07C 213/02; C07C 219/06; C07C 67/08; C07C 67/24
See application file for complete search history.

(56) References Cited

U.S. PATENT DOCUMENTS

| 3,366,688 A | * | 1/1968 | Hargrove ............. C07C 215/08 546/193 |
| 3,845,214 A | | 10/1974 | Gallo et al. |
| 10,144,701 B2 | | 12/2018 | Tang et al. |
| 2018/0029973 A1 | | 2/2018 | Tang |

FOREIGN PATENT DOCUMENTS

| CN | 1173867 | 2/1998 |
| CN | 1516690 | 7/2004 |
| CN | 104829465 | 8/2015 |
| WO | 2012081978 | 6/2012 |

OTHER PUBLICATIONS

Tang, Fanghui; Final Office Action for U.S. Appl. No. 15/552,772, filed Aug. 22, 2017, dated Jul. 6, 2018, 7 pgs.
Tang, Fanghui; Issue Notification for U.S. Appl. No. 15/552,772, filed Aug. 22, 2017, dated Nov. 14, 2018, 1 pg.
Tang, Fanghui; Non-Final Office Action for U.S. Appl. No. 15/552,772, filed Aug. 22, 2017, dated Feb. 7, 2018, 1 pgs.
Tang, Fanghui; Notice of Allowance for U.S. Appl. No. 15/552,772, filed Aug. 22, 2017, dated Aug. 10, 2018, 10 pgs.
Tang, Fanghui; Restriction Requirement for U.S. Appl. No. 15/552,772, filed Aug. 22, 2017, dated Jan. 10, 2018, 7 pgs.
Tang, Fanghui; International Preliminary Report on Patentability for serial No. PCT/CN2016/000180, filed Mar. 31, 2016, dated Oct. 10, 2017, 11 pgs.
Tang, Fanghui; International Search Report and Written Opinion for serial No. PCT/CN2016/000180, filed Mar. 31, 2016, dated Jun. 29, 2016, 17 pgs.
Wang, Y.H., et al., "Reductive hydroxyalkylation/alkylation of amines with lactones/esters," Organic Biomolecular Chemistry, vol. 10, No. 32, Dec. 31, 2013, pp. 6504-6511.

* cited by examiner

*Primary Examiner* — Pancham Bakshi
*Assistant Examiner* — Mark R Luderer
(74) *Attorney, Agent, or Firm* — Taylor English Duma LLP; Zhaoyang Li

(57) ABSTRACT

The present invention relates to a preparation method of 4-isopropylamino-1-butanol, in which using cheap and readily available tetrahydrofuran and acetic acid solution of hydrogen bromide as starting materials to prepare a novel intermediate of 4-isopropylamino-1-acetoxyl butane and further obtain the target product. The present invention has advantages of convenient process operations, mild reaction conditions, economical and environment-friendly benefits, and suitability for industrial production to obtain the product with high purity and high yield.

1 Claim, No Drawings

METHOD OF PREPARATION OF 4-ISOPROPYLAMINO-1-BUTANOL

CROSS-REFERENCE TO RELATED APPLICATIONS

The present invention is a divisional application of U.S. application Ser. No. 15/552,772, filed Aug. 22, 2017, which is a U.S. national phase of International Application No. PCT/CN2016/000180 under 35 U.S.C. § 371. The teaching in these related applications are incorporated herein in its entirety by reference.

FIELD OF THE INVENTION

The present invention relates to the technical field of chemical synthesis in pharmaceutical industry, specifically, it relates to a preparation method of 4-isopropylamino-1-butanol and a novel intermediate thereof.

BACKGROUND 4-isopropylamino-1-butanol is an important intermediate in pharmaceutical industry, and its structural formula is represented by formula (I):

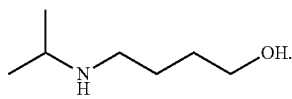

(I)

4-isopropylamino-1-butanol was widely used in the pharmaceutical synthesis, for example, Patent Document WO2002088084A1 disclosed a four-step reaction using 4-isopropylamino-1-butanol as the raw material to prepare pulmonary hypertension drug of selexipag. This document was incorporated by reference into the present application.

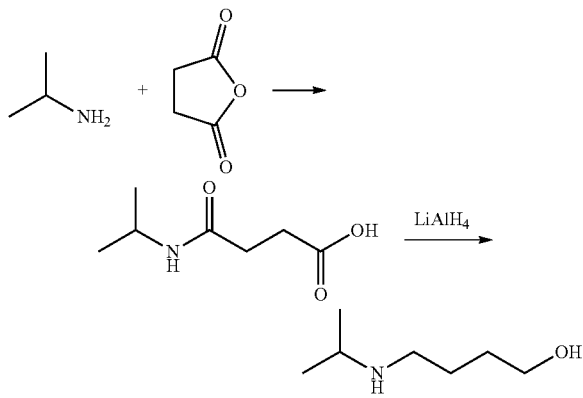

Journal of Organic Chemistry (1961), Vol. 26, P 1744-1747 disclosed a preparation method of 4-isopropylamino-1-butanol, which comprised: (1) reacted succinic anhydride with isopropyl amine to obtain 3-isopropyl carbamoyl propionic acid; (2) reduced 3-isopropylcarbamoyl propionic acid with lithium aluminum hydride to obtain 4-isopropylamino-1-butanol.

This method had defects: lithium aluminum hydride was expensive, large consumed and high cost; lithium aluminum hydride was also a strong reducing agent with great security risks, when it meets water, explosion may be happened, so there were strict requirements for the water contents of the solvents; the yield was low; a large amount of waste water containing aluminum was produced, post-treatment was complicated, and this method was unsuitable for industrial production.

Organic and Biomolecular Chemistry (2012), Vol. 10, P 6504-6511 disclosed a preparation method of 4-isopropylamino-1-butanol, which comprised: a reduction reaction was carried out between DIBAL-H.i-PrNH2 and γ-butyrolactone in a hexane solution of diisobutylaluminium hydride (DIBAL-H) to obtain 4-isopropylamino-1-butanol. The reaction formula was shown below:

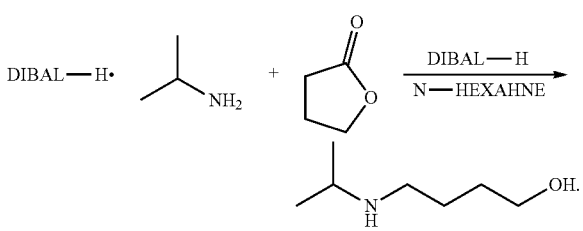

This method had defects: DIBAL-H.i-PrNH2 was needed to be prepared freshly; DIBAL-H was expensive and unstable so only its hexane solution could be used; column chromatography was used in the post-treatment; a large amount of waste water containing aluminum was produced, and this method was unsuitable for industrial production.

European Patent Document EP1400518A1 disclosed a synthesis method for 4-isopropylamino-1-butanol, which comprised: reacted 4-aminobutanol with acetone in ethanol, then kept a hydrogenation reaction at 2-3 atmospheres for 48 hours under catalyzing of platinum oxide to obtain 4-isopropylamino-1-butanol. The reaction formula was shown below:

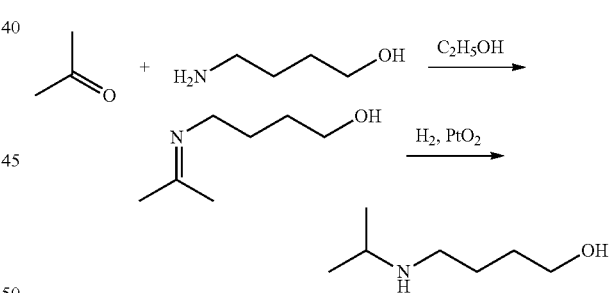

In this process, 4-aminobutanol and platinum oxide were expensive, special high-pressure hydrogenation equipment was needed, so its industrial application was limited.

Therefore, there still had some defects in the known preparation methods of 4-isopropylamino-1-butanol in the conventional methods, it was necessary to develop novel preparation methods thereof.

SUMMARY OF THE INVENTION

The objective of the present invention is to provide a novel synthesis route of 4-isopropylamino-1-butanol represented by formula (I), which will benefit for process feasibility, safety and environmental protection, obtaining a product with low cost and high quality, and suitability for industrial production.

According to the objective of the present invention, a preparation method of 4-isopropylamino-1-butanol represented by formula (I) is provided, which comprising the following steps:

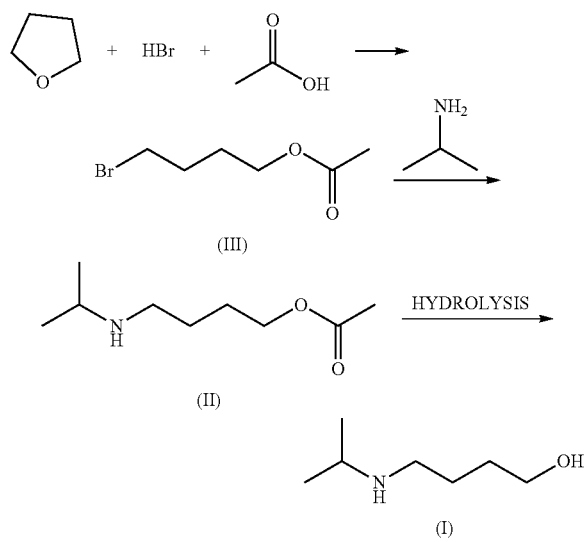

(1) reacting tetrahydrofuran with an acetic acid solution of hydrogen bromide to obtain 4-bromo-1-acetoxyl butane represented by formula (III);

(2) reacting 4-bromo-1-acetoxyl butane represented by formula (III) with isopropyl amine to obtain 4-isopropylamino-1-acetoxyl butane represented by formula (II); and (3) hydrolyzing 4-isopropylamino-1-acetoxyl butane represented by formula (II) to obtain 4-isopropylamino-1-butanol represented by formula (I).

In the step (1), the mass content of hydrogen bromide in the acetic acid solution of hydrogen bromide is 10% to 40%; preferably, 33% or 40%, because such kind of solution is readily available commercially.

In the step (1), the molar ratio of tetrahydrofuran to hydrogen bromide is 1:1 to 50:1; preferably, 2:1 to 15:1; more preferably, 2:1 to 5:1.

In the step (1), the reaction temperature is 0 to 50° C.; preferably, 10 to 25° C.

After completion of the step (1), 4-bromo-1-acetoxyl butane (III) was collected by vacuum distillation, and the excess tetrahydrofuran and acetic acid were recovered.

In the step (1), the process is feasible with low cost and simple operations, the yield of 4-bromo-1-acetoxyl butane (III) is high and its gas chromatographic purity is up to 99.5%.

In the step (2), the molar ratio of isopropyl amine to 4-bromo-1-acetoxyl butane (III) is 1:1 to 10:1; preferably, 2:1 to 5:1.

The step (2) reaction can be carried out in the presence of an alkali so as to accelerate the reaction rate, moderate the reaction conditions, simplify the post-treatment and improve the yield. The alkali is selected from the group consisting of carbonates, bicarbonates, phosphates, hydrophosphates and organic amines; preferably, the alkali is selected from the group consisting of sodium carbonate, potassium carbonate, sodium bicarbonate, sodium phosphate, potassium phosphate, potassium hydrophosphate, triethylamine, pyridine, diisopropylethylamine and isopropylamine.

The reaction solvent of the step (2) is selected from the group consisting of chlorinated alkanes, alcohols, strong polar aprotic solvents and non-polar aprotic solvents; preferably, the reaction solvent of the step (2) is selected from the group consisting of dichloromethane, acetonitrile, ethanol, ethyl acetate and N,N-dimethyl formamide.

The reaction temperature of the step (2) is 0 to 50° C.; preferably, 0 to 30° C.

After completion of the step (2), 4-isopropylamino-1-acetoxyl butane (II) can be collected by filtration, concentration or extraction, further be purified by recrystallization.

In the step (3), the hydrolyzing reaction can be carried out in the presence of an acid. The acid, for example, is sulfuric acid or p-toluenesulfonic acid.

Preferably, the hydrolyzing reaction of the step (3) is carried out in the presence of an alkali, which will benefit for acceleration of reaction rate, improvement of reaction selectivity, simplification of the post-treatment and producing a product with high purity and high yield. The alkali is selected from the group consisting of sodium hydroxide, potassium hydroxide and lithium hydroxide. The molar ratio of 4-isopropylamino-1-acetoxyl butane to the alkali is 1:1 to 1:5, preferably, 1:1 to 1:2.

In the step (3), the solvent of the hydrolyzing reaction is selected from the group consisting of water, C1-4 alcohols and the mixtures thereof; preferably, the solvent of the hydrolyzing reaction is selected from the group consisting of methanol, ethanol and water.

In the step (3), the temperature of the hydrolyzing reaction is −20 to 80° C.; preferably, 0 to 30° C.

After completion of the step (3), the product can be separated and purified by normal methods in the field, for example, filtration, concentration, extraction or distillation.

The product, 4-isopropylamino-1-butanol, has high yield and its gas chromatographic purity is up to ≥99.5%, which will satisfy the requirements for high quality intermediates in the pharmaceutical industry so as to benefit for the subsequent synthesis reactions and obtain drugs with high quality and high yield. Especially, for the multi-step synthesis of pulmonary hypertension drug of selexipag, it is needed to use 4-isopropylamino-1-butanol with high quality and high yield prepared by the present invention.

In addition, the present invention provides a novel intermediate of 4-isopropylamino-1-acetoxyl butane represented by formula (II). It is a key intermediate in the preparation of 4-isopropylamino-1-butanol (I).

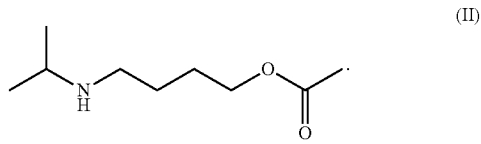

Compared with conventional methods, the present invention provides a novel preparation method of 4-isopropylamino-1-butanol, in which using cheap and readily available tetrahydrofuran and acetic acid solution of hydrogen bromide as starting materials to prepare a novel intermediate of 4-isopropylamino-1-acetoxyl butane and further obtain 4-isopropylamino-1-butanol. This feasible synthesis route has simple operations, mild reaction conditions and low cost, it is environmentally friendly, and no special equipment is needed. The product with high purity and high yield is suitable for being used in the drug synthesis and industrial production.

EXAMPLES

The following examples describe the preparation method of the present invention in details. Those examples will help to further understand the present invention, but not be used to restrict the scope of the present invention.

Raw materials and reagents used in the examples are commercially available.

Analysis methods in the present invention:

Gas chromatography (GC) detection uses Agilent 7890A Gas Chromatograph.

Proton nuclear magnetic resonance spectras (1H-NMR) are recorded on a 400 MHz FT-NMR spectrometer, Bruker Avance 400, Bruker Corporation.

Example 1: Preparation of 4-bromo-1-acetoxyl butane 185 mL of tetrahydrofuran was added to a 500 mL four-neck flask and cooled to 10° C. by ice-water bath, 280 g acetic acid solution of hydrogen bromide with its mass content of 33% was added dropwise, then the mixture was heated to 25° C. and reacted at this temperature for 2 hours until the reaction was completed.

Tetrahydrofuran and acetic acid were recovered by vacuum distillation, the residue was heated to 100° C. and distilled at 2 mmHg vacuum, then 87 to 89° C. component fraction was collected to obtain 200 g of colorless clear liquid of 4-bromo-1-acetoxyl butane. The molar yield: 90%, GC purity: 99.5%.

$^1$H-NMR data: (400 MHz, CDCl3) δ: 4.05 (t, J=6.4 Hz, 2H), 3.39 (t, J=6.8 Hz, 2H), 1.99 (s, 3H), 1.86 (m, 2H), 1.75 (m, 2H).

Example 2: Preparation of 4-bromo-1-acetoxyl butane 460 mL of tetrahydrofuran was added to a 1000 mL four-neck flask and cooled to 10° C. by ice-water bath, 280 g acetic acid solution of hydrogen bromide with its mass content of 33% was added dropwise, then the mixture was kept at 10° C. for 4 hours to react until the reaction was completed.

Tetrahydrofuran and acetic acid were recovered by vacuum distillation, the residue was heated to 100° C. and distilled at 2 mmHg vacuum, then 87 to 89° C. component fraction was collected to obtain 206 g of colorless clear liquid of 4-bromo-1-acetoxyl butane. The molar yield: 93%, GC purity: 99.5%.

$^1$H-NMR data: (400 MHz, CDCl3) δ: 4.05 (t, J=6.4 Hz, 2H), 3.39 (t, J=6.8 Hz, 2H), 1.99 (s, 3H), 1.86 (m, 2H), 1.75 (m, 2H).

Example 3: Preparation of 4-bromo-1-acetoxyl butane 93 mL of tetrahydrofuran was added to a 1000 mL four-neck flask and cooled to 10° C. by ice-water bath, 230 g acetic acid solution of hydrogen bromide with its mass content of 40% was added dropwise, then the mixture was kept at 10° C. for 3 hours to react until the reaction was completed.

Tetrahydrofuran and acetic acid were recovered by vacuum distillation, the residue was heated to 100° C. and distilled at 2 mmHg vacuum, then 87 to 89° C. component fraction was collected to obtain 184 g of colorless clear liquid of 4-bromo-1-acetoxyl butane. The molar yield: 83%, GC purity: 99.5%.

$^1$H-NMR data: (400 MHz, CDCl3) δ: 4.05 (t, J=6.4 Hz, 2H), 3.39 (t, J=6.8 Hz, 2H), 1.99 (s, 3H), 1.86 (m, 2H), 1.75 (m, 2H).

Example 4: Preparation of 4-bromo-1-acetoxyl butane 185 mL of tetrahydrofuran was added to a 2000 mL four-neck flask and cooled to 20° C. by ice-water bath, 920 g acetic acid solution of hydrogen bromide with its mass content of 10% was added dropwise, then the mixture was heated to 50° C. and reacted for 3 hours until the reaction was completed.

Tetrahydrofuran and acetic acid were recovered by vacuum distillation, the residue was heated to 100° C. and distilled at 2 mmHg vacuum, then 87 to 89° C. component fraction was collected to obtain 194 g of colorless clear liquid of 4-bromo-1-acetoxyl butane. The molar yield: 87%, GC purity: 99.5%.

$^1$H-NMR data: (400 MHz, CDCl3) δ: 4.05 (t, J=6.4 Hz, 2H), 3.39 (t, J=6.8 Hz, 2H), 1.99 (s, 3H), 1.86 (m, 2H), 1.75 (m, 2H).

Example 5: Preparation of 4-isopropylamino-1-acetoxyl butane 39 g of 4-bromo-1-acetoxyl butane, 250 mL of acetonitrile and 100 g of sodium bicarbonate were added to a 500 mL four-neck flask and cooled to 5° C. by ice-water bath, 35.4 g of isopropyl amine was added dropwise, then the mixture was heated to 20° C. and reacted for 5 hours until the reaction was completed.

Inorganic salts were removed by filtration, the filtrate was concentrated to recover acetonitrile, 300 mL of ethyl acetate was added to the residue to recrystallize, and 31.8 g of 4-isopropylamino-1-acetoxyl butane was obtained. The molar yield was 92%.

$^1$H-NMR data: (400 MHz, CDCl3) δ: 4.02 (t, J=6.8 Hz, 2H), 2.74 (m, 1H), 2.57 (t, J=7.2 Hz, 2H), 1.97 (s, 3H), 1.62 (m, 2H), 1.49 (m, 2H), 0.99 (d, J=6.0 Hz, 6H).

Example 6: Preparation of 4-isopropylamino-1-acetoxyl butane 39 g of 4-bromo-1-acetoxyl butane, 250 mL of acetonitrile and 100 g of sodium bicarbonate were added to a 500 mL four-neck flask, 11.5 g of isopropyl amine was added dropwise, then the mixture was heated to 50° C. and reacted for 2 hours until the reaction was completed.

Inorganic salts were removed by filtration, the filtrate was concentrated to recover acetonitrile, 300 mL of ethyl acetate was added to the residue to recrystallize, and 28.7 g of 4-isopropylamino-1-acetoxyl butane was obtained. The molar yield was 83%.

$^1$H-NMR data: (400 MHz, CDCl3) δ: 4.02 (t, J=6.8 Hz, 2H), 2.74 (m, 1H), 2.57 (t, J=7.2Hz, 2H), 1.97 (s, 3H), 1.62 (m, 2H), 1.49 (m, 2H), 0.99 (d, J=6.0 Hz, 6H).

Example 7: Preparation of 4-isopropylamino-1-acetoxyl butane 39 g of 4-bromo-1-acetoxyl butane, 200 mL of dichloromethane and 25 g of triethylamine were added to a 500 mL four-neck flask and cooled to 10° C., 23 g of isopropyl amine was added dropwise, then the mixture was kept at this temperature for 2 hours to react until the reaction was completed.

50 mL of water was added to wash, the organic phase was concentrated to recover dichloromethane, 200 mL of ethyl acetate was added to the residue to recrystallize, and 30.5 g of 4-isopropylamino-1-acetoxyl butane was obtained. The molar yield was 83%.

$^1$H-NMR data: (400 MHz, CDCl3) δ: 4.02 (t, J=6.8 Hz, 2H), 2.74 (m, 1H), 2.57 (t, J=7.2 Hz, 2H), 1.97 (s, 3H), 1.62 (m, 2H), 1.49 (m, 2H), 0.99 (d, J=6.0 Hz, 6H).

Example 8: Preparation of 4-isopropylamino-1-acetoxyl butane 39 g of 4-bromo-1-acetoxyl butane and 250 mL of ethyl acetate were added to a 500 mL four-neck flask, 115 g of isopropyl amine was added dropwise, then the mixture was heated to 20° C. and reacted for 5 hours until the reaction was completed.

50 mL of water was added, the mixture was stirred for 10 minutes, filtered and dried to obtain 30 g of 4-isopropylamino-1-acetoxyl butane. The molar yield was 87%.

$^1$H-NMR data: (400 MHz, CDCl3) δ: 4.02 (t, J=6.8 Hz, 2H), 2.74 (m, 1H), 2.57 (t, J=7.2 Hz, 2H), 1.97 (s, 3H), 1.62 (m, 2H), 1.49 (m, 2H), 0.99 (d, J=6.0 Hz, 6H).

Example 9: Preparation of 4-isopropylamino-1-acetoxyl butane 39 g of 4-bromo-1-acetoxyl butane, 250 mL of acetonitrile and 100 g of sodium bicarbonate were added to a 500 mL four-neck flask, 57.5 g of isopropyl amine was added dropwise, then the mixture was heated to 30° C. and reacted for 5 hours until the reaction was completed.

Inorganic salts were removed by filtration, the filtrate was concentrated to recover acetonitrile, 300 mL of ethyl acetate was added to the residue to recrystallize, and 29.4 g of 4-isopropylamino-1-acetoxyl butane was obtained. The molar yield was 88%.

$^1$H-NMR data: (400 MHz, CDCl3) δ: 4.02 (t, J=6.8 Hz, 2H), 2.74 (m, 1H), 2.57 (t, J=7.2 Hz, 2H), 1.97 (s, 3H), 1.62 (m, 2H), 1.49 (m, 2H), 0.99 (d, J=6.0 Hz, 6H).

Example 10: Preparation of 4-isopropylamino-1-butanol 34 g of 4-isopropylamino-1-acetoxyl butane and 200 mL of ethanol were added to a 250 mL three-neck flask, a solution containing 8 g of sodium hydroxide dissolved in 20 mL of water was added dropwise while the temperature was maintained 10° C., then the mixture was stirred at 20° C. for 2 hours to react until the reaction was completed.

Ethanol was recovered by concentration, 200 mL of dichloromethane and 100 mL of water were added to the residue to extract, the organic phase was dried by sodium sulfate and dichloromethane was recovered by concentration, then the residue was distilled at 1 mmHg vacuum and 83 to 85° C. component fraction was collected to obtain 24.7 g of 4-isopropylamino-1-butanol (this product will be solidified in the environment of the temperature below 10° C.). The molar yield: 95%, GC purity: 99.5%.

$^1$H-NMR data: (400 MHz, CDCl3) δ: 3.51 (t, J=5.2 Hz, 2H), 2.76 (m, 1H), 2.58 (t, J=5.6 Hz, 2H), 1.62 (m, 2H), 1.55 (m, 2H), 1.02 (d, J=6.4 Hz, 6H).

Example 11: Preparation of 4-isopropylamino-1-butanol 34 g of 4-isopropylamino-1-acetoxyl butane and 200 mL of ethanol were added to a 250 mL three-neck flask, a solution containing 16 g of sodium hydroxide dissolved in 20 mL of water was added dropwise while the temperature was maintained 0° C., then the mixture was stirred at 30° C. for 1 hour to react until the reaction was completed.

Ethanol was recovered by concentration, 200 mL of dichloromethane and 100 mL of water were added to the residue to extract, the organic phase was dried by sodium sulfate and dichloromethane was recovered by concentration, then the residue was distilled at 1 mmHg vacuum and 83 to 85° C. component fraction was collected to obtain 22.6 g of 4-isopropylamino-1-butanol. The molar yield: 87%, GC purity: 99.5%.

$^1$H-NMR data: (400 MHz, CDCl3) δ: 3.51 (t, J=5.2 Hz, 2H), 2.76 (m, 1H), 2.58 (t, J=5.6 Hz, 2H), 1.62 (m, 2H), 1.55 (m, 2H), 1.02 (d, J=6.4 Hz, 6H).

Example 12: Preparation of 4-isopropylamino-1-butanol 34 g of 4-isopropylamino-1-acetoxyl butane and 200 mL of ethanol were added to a 250 mL three-neck flask, a solution containing 40 g of sodium hydroxide dissolved in 50 mL of water was added dropwise while the temperature was maintained −20° C., then the mixture was stirred at 10° C. for 1 hour to react until the reaction was completed.

Ethanol was recovered by concentration, 200 mL of dichloromethane and 100 mL of water were added to the residue to extract, the organic phase was dried by sodium sulfate and dichloromethane was recovered by concentration, then the residue was distilled at 1 mmHg vacuum and 83 to 85° C. component fraction was collected to obtain 22.1 g of 4-isopropylamino-1-butanol. The molar yield: 85%, GC purity: 99.7%.

$^1$H-NMR data: (400 MHz, CDCl3) δ: 3.51 (t, J=5.2 Hz, 2H), 2.76 (m, 1H), 2.58 (t, J=5.6 Hz, 2H), 1.62 (m, 2H), 1.55 (m, 2H), 1.02 (d, J=6.4 Hz, 6H).

What is claimed is:

1. 4-isopropylamino-1-acetoxyl butane represented by formula (II):

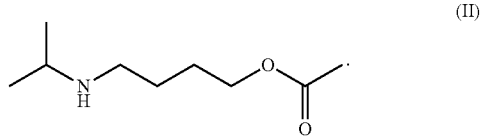

(II)

* * * * *